(12) United States Patent
Miyazaki (10) Patent No.: US 9,042,961 B2
(45) Date of Patent: May 26, 2015

(54) VELOCITY MEASUREMENT OF MR-IMAGED FLUID FLOWS

(75) Inventor: Mitsue Miyazaki, Mount Prospect, IL (US)

(73) Assignees: KABUSHIKI KAISHA TOSHIBA, Tokyo (JP); TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 342 days.

(21) Appl. No.: 12/923,894

(22) Filed: Oct. 13, 2010

(65) Prior Publication Data

US 2012/0095326 A1    Apr. 19, 2012

(51) Int. Cl.
*A61B 5/05* (2006.01)
*A61B 5/055* (2006.01)
*G01R 33/483* (2006.01)
*G01R 33/563* (2006.01)

(52) U.S. Cl.
CPC ............ *A61B 5/055* (2013.01); *G01R 33/4838* (2013.01); *G01R 33/56308* (2013.01)

(58) Field of Classification Search
USPC ........................... 600/407, 410–423; 324/306
See application file for complete search history.

(56) References Cited

U.S. PATENT DOCUMENTS

| 5,315,248 | A  |   | 5/1994  | Yamaguchi      |         |
|-----------|----|---|---------|----------------|---------|
| 5,684,398 | A  | * | 11/1997 | Takiguchi et al. | 324/306 |
| 6,760,611 | B1 |   | 7/2004  | Watanabe       |         |
| 6,801,800 | B2 | * | 10/2004 | Miyazaki et al. | 600/410 |

| 2008/0009705 | A1 |   | 1/2008  | Furudate       |         |
|--------------|----|---|---------|----------------|---------|
| 2008/0061780 | A1 | * | 3/2008  | Yamada et al.  | 324/309 |
| 2008/0161678 | A1 | * | 7/2008  | Miyazaki et al. | 600/419 |
| 2009/0143667 | A1 | * | 6/2009  | Kovacs et al.  | 600/410 |
| 2009/0148020 | A1 |   | 6/2009  | Sugiura        |         |
| 2009/0245607 | A1 |   | 10/2009 | Sugiura        |         |
| 2009/0309592 | A1 |   | 12/2009 | Furudate       |         |
| 2010/0198053 | A1 |   | 8/2010  | Miyazaki et al. |        |

FOREIGN PATENT DOCUMENTS

| CN | 101444419 A | 6/2009 |
| JP | H01-238851  | 9/1989 |
| JP | H02-255124  | 10/1990 |
| JP | H06-022934  | 2/1994 |
| JP | H07-116143  | 5/1995 |

(Continued)

OTHER PUBLICATIONS

Miyazaki, et al., "Non-contrast-enhanced MR angiography using 3D ECG-synchronized half-Fourier fast spin echo," *JMRI* 12:776-783 (2000).

(Continued)

*Primary Examiner* — James Kish
(74) *Attorney, Agent, or Firm* — Nixon & Vanderhye P.C.

(57) ABSTRACT

Velocity of MR-imaged fluid flows is measured. Data representing a measure of distance traveled by flowing fluid appearing in at least two MR images of a subject's tissue taken at different respective imaging times is generated. Data representing at least one fluid velocity measurement of the flowing fluid is generated by calculating at least one instance of distance traveled by the fluid divided by elapsed time during travel based on different respective imaging times. Data representing at least one fluid velocity measurement is then output to at least one of: (a) a display screen, (b) a non-transitory data storage medium, and (c) a remotely located site.

18 Claims, 9 Drawing Sheets

(56) References Cited

FOREIGN PATENT DOCUMENTS

| JP | 2004-329614 | 11/2004 |
|---|---|---|
| JP | 2008-23317 A | 2/2008 |
| JP | 2009-247773 | 10/2009 |
| JP | 2010-022813 | 2/2010 |
| JP | 2010-051835 | 3/2010 |
| JP | 2010-201154 | 9/2010 |
| JP | 2010-201184 | 9/2010 |

OTHER PUBLICATIONS

Suga, et al., Lung perfusion impairments in pulmonary embolic and airway obstruction with noncontrast MR imaging, *J Appl Physiol* 92:2439-2451 (2002).

Takahashi, et al., "Non-contrast-enhanced renal MRA using time-spatial labeling pulse (t-SLIP) with 3D balanced SSFP," presented at the ISMRM 15th Annual Meeting, Berlin, Germany, p. 179 (2007).

Yamamoto, et al., "Non-contrast-enhanced MRDSM of peripheral arteries using continuous acquisitions of ECG-triggered 2D half-Fourier FSE within a cardiac cycle," presented at the ISMRM 12th Annual Meeting, Toronto, Canada, p. 1709 (2003).

Kanazawa, et al., "Time-spatial labeling inversion tag (t-SLIT) using a selective IR-tag on/off pulse in 2D and 3D half-Fourier FSE as arterial spin labeling," presented at the ISMRM 10th Annual Meeting, Hawaii, p. 140 (2002).

Furudate, et al., "FBI-Navi for Easy Determination of Diastolic and Systolic Triggering Phases in Non-Contrast Fresh Blood Imaging (FBI)," ISMRM 16th Annual Meeting, Toronto, Canada, p. 2902 (2008).

International Search Report mailed Nov. 15, 2011 in PCT/JP2011/073568.

Office Action mailed Dec. 9, 2013 in CN 201180003249.2.

Office Action dated Dec. 12, 2014 in U.S. Appl. No. 13/644,338.

Extended European Search Report dated Mar. 12, 2015 in EP 11832599.2.

Zhang H. L. et al., "Body Magnetic Resonance Angiography," Seminars in Roentgenology, W.B. Saunders, US, vol. 44, No. 2, Apr. 1, 2009, pp. 84-98, XP026017913, ISSN: 0037-198X.

\* cited by examiner

VELOCITY MEASUREMENT OF MR-IMAGED FLUID FLOWS

FIELD

The subject matter below relates generally to magnetic resonance imaging (MRI) processes. More particularly, velocity of MR-imaged fluid flow is measured.

DETAILED DESCRIPTION

Figure 1:
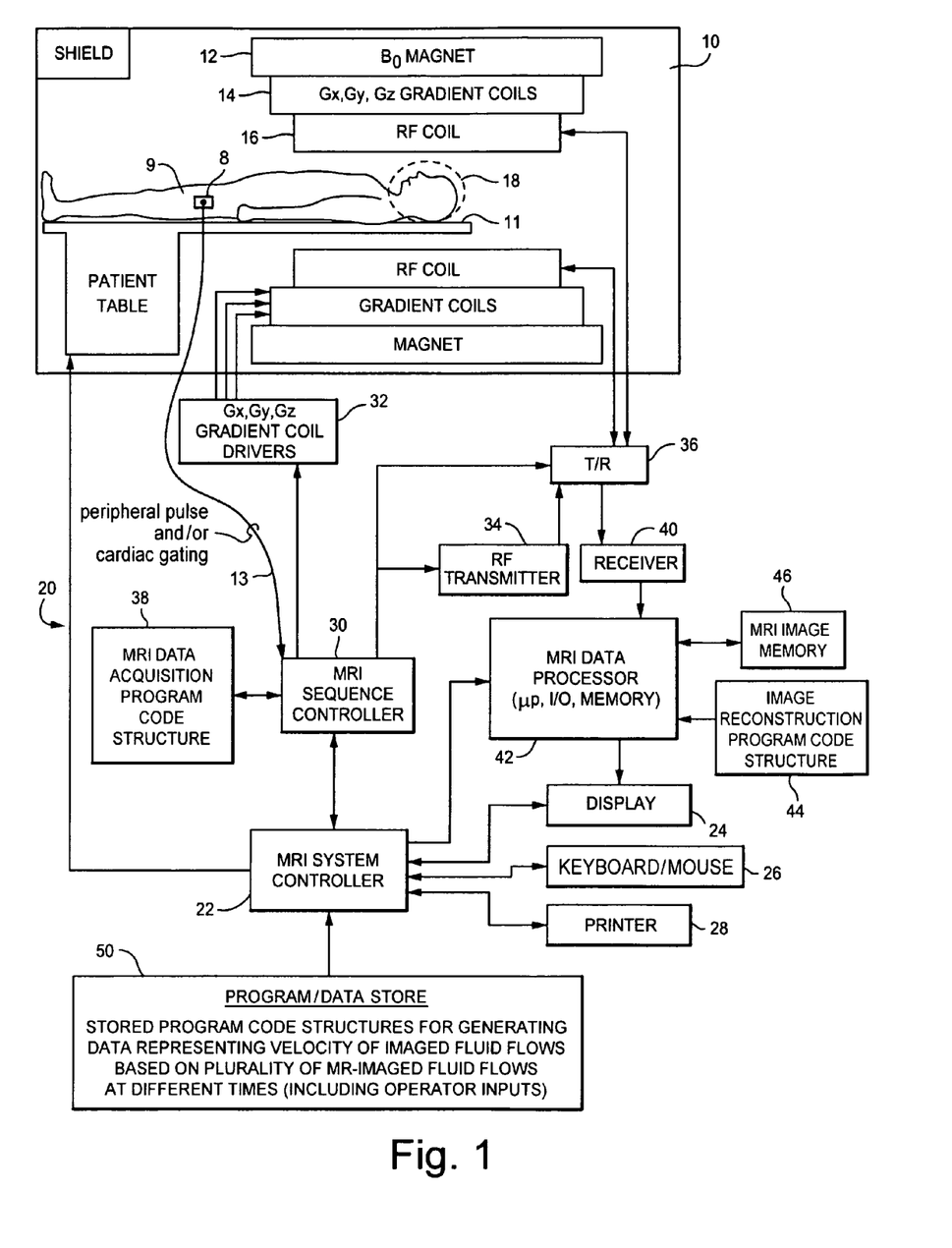
FIG. 1 is a high-level schematic block diagram of an MRI system adapted to acquire and process data for MRI and/or to process MR images of flowing fluid(s) in an imaged patient volume and generate data for storage and/or display representing the velocity of such fluid(s)

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field BO magnet 12, a $G_x$, $G_y$ and $G_z$ gradient coil set 14 and an RF coil assembly 16. Along the horizontal axis of this cylindrical array of elements is an imaging volume 18 shown as substantially encompassing the head of a patient 9 supported by a patient table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$ and $G_z$ gradient coil drivers 32, as well as the RF transmitter 34 and the transmit/receive switch 36 (if the same RF coil is used for both transmission and reception). The MRI sequence controller 30 includes suitable program code structure 38 for implementing MRI data acquisition sequences (including the imaging of flowing fluid such as blood) already available in the repertoire of the MRI sequence controller 30. Cardiac signal acquisition apparatus 8 (e.g., ECG or peripheral pulse transducer(s) coupled appropriately to the body of patient 9) may be used to provide cardiac gating signals 13 to trigger the MRI sequence controller 30.

The MRI system 20 includes an RF receiver 40 providing input to data processor 42 so as to create processed image data to display 24. The MRI data processor 42 is also configured for access to image reconstruction program code structure 44 and to MR image memory 46 (e.g., for storing MRI data derived from processing in accordance with the exemplary embodiments and the image reconstruction program code structure 44).

Also illustrated in FIG. 1 is a generalized depiction of an MRI system program/data store 50 where stored program code structures (e.g., for image reconstruction and for flow velocity distance/time measurements, operator inputs to same, etc.) are stored in computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR-imaging reconstruction process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the blood flowing in arteries of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, causes a particular sequence of operational states to occur and be transitioned through within the MRI system.

The exemplary embodiments described below provide improved ways to process data acquisitions and/or to generate and display MR-images, including the velocity of flowing fluids depicted therein.

MR signal strength changes between images gated in synchronism with cardiac systolic and diastolic timings can be used to obtain non-contrast agent time-resolved fluid (e.g., blood) flow by subtracting the dark systole image from the bright diastole image and/or vice versa. This is sometimes referred to as time-resolved non-contrast MRA (magnetic resonance angiography). In addition, there are other known non-contrast agent imaging techniques for fluid flows such as time-SLIP (spatial labeling inversion pulse) sequences sometimes referred to as arterial spin labeling (ASL).

An operator interface to facilitate measuring fluid flow velocities in these non-contrast imaging techniques would be desirable.

In accordance with exemplary embodiments to be described below, fluid flow velocity measurements in non-contrast flow images can be achieved in at least two ways. First, with diastolic-systolic subtraction images, the displacement distance between MR signals emanating from fluid flows can be ascertained. For example, if a relatively linear artery path is involved, then a simple line from a start point to an end point may suffice. Alternatively, even a tortuous path may be drawn by connecting strategically placed points along the displacement path. Automatic tracking of distance traveled by flowing fluid along an arbitrarily-shaped path may also be made available. In any event, the distance along which flowing fluid has passed between successive image times can be used to calculate specific velocity between successive image times, as well as average or mean velocity over a succession of such image times.

If a non-contrast time-SLIP image technique is used, it may involve somewhat different imaging sequences such as FASE (fast asymmetric spin echo) or bSSFP (balanced steady state free precession) in either centric ordering of phase encoding for k-space or sequential ordering of phase encoding for k-space. The numerator is, of course, still the distance traveled by the signal-producing and flowing material (e.g., blood). The time increment to be used for the denominator (i.e., blood travel time) in calculating mean velocity can be BBTI (black-blood time to inversion) plus the effective time to echo (TEeff) for time-SLIP with FASE imaging. The time increment for the denominator would be simply BBTI for time-SLIP with bSSFP in centric phase encoding ordering for k-space. The relevant time increment to use with time-SLIP with bSSFP in sequential phase encoding ordering for k-space is BBTI plus one-half ETL (echo train length).

Velocity measurements may be made for MR signal producing flow displacements between different ECG (electrocardiogram gating) signal points (for example, systole to diastole) or using FB-Navi (fresh blood-navigation) signal difference plots. Velocity measurement of flowing MR signal displacements or traveled MR signals can be measured.

As just mentioned, displacements of MR signal producing flows using time-SLIP imaging techniques during BBTI (possibly plus TEeff, and/or ETL/2 depending on k-space ordering) can also be used to calculate mean velocity.

In an exemplary embodiment, a simple graphical user interface (GUI) may be used (e.g., by depression of a mouse button) to selectively calculate flow velocity along a traveled distance. The traveled distance may be outlined by the user (e.g., by defining strategically placed points along the path) or by a system-provided auto-tracking facility. In any event, the distance traveled is then divided by the time interval associated with that distance (e.g., between subtracted images in ECG delayed imaging techniques and/or in time-SLIP imaging techniques).

The graphical user interface (GUI) can be used to measure flow movements of mean velocity and/or specific velocity. In non-contrast techniques, velocity measurements can be measured in at least two ways. First, using diastolic-systolic subtraction imaging techniques, a displacement line can be drawn along the distance of MR signal displacement (by nearest point or line connected in length). The MRI display system may automatically record this as a distance and then, by clicking an appropriate button (e.g., or a right mouse click to select velocity) calculation of such distance divided by an appropriate corresponding time difference (e.g., between the effective taking times of the subtracted systolic and diastolic images) can be achieved. In a second method (e.g., a spin labeling method), MRI signal producing flow travel from the start to the last signal in distance divided by the (BBTI+TEeff) for time-SLIP with FASE and (BBTI) for time-slip with bSSFP in centric ordering and (BBTI+ETL/2 for time-SLIP with bSSFP in sequential ordering).

Figure 2:
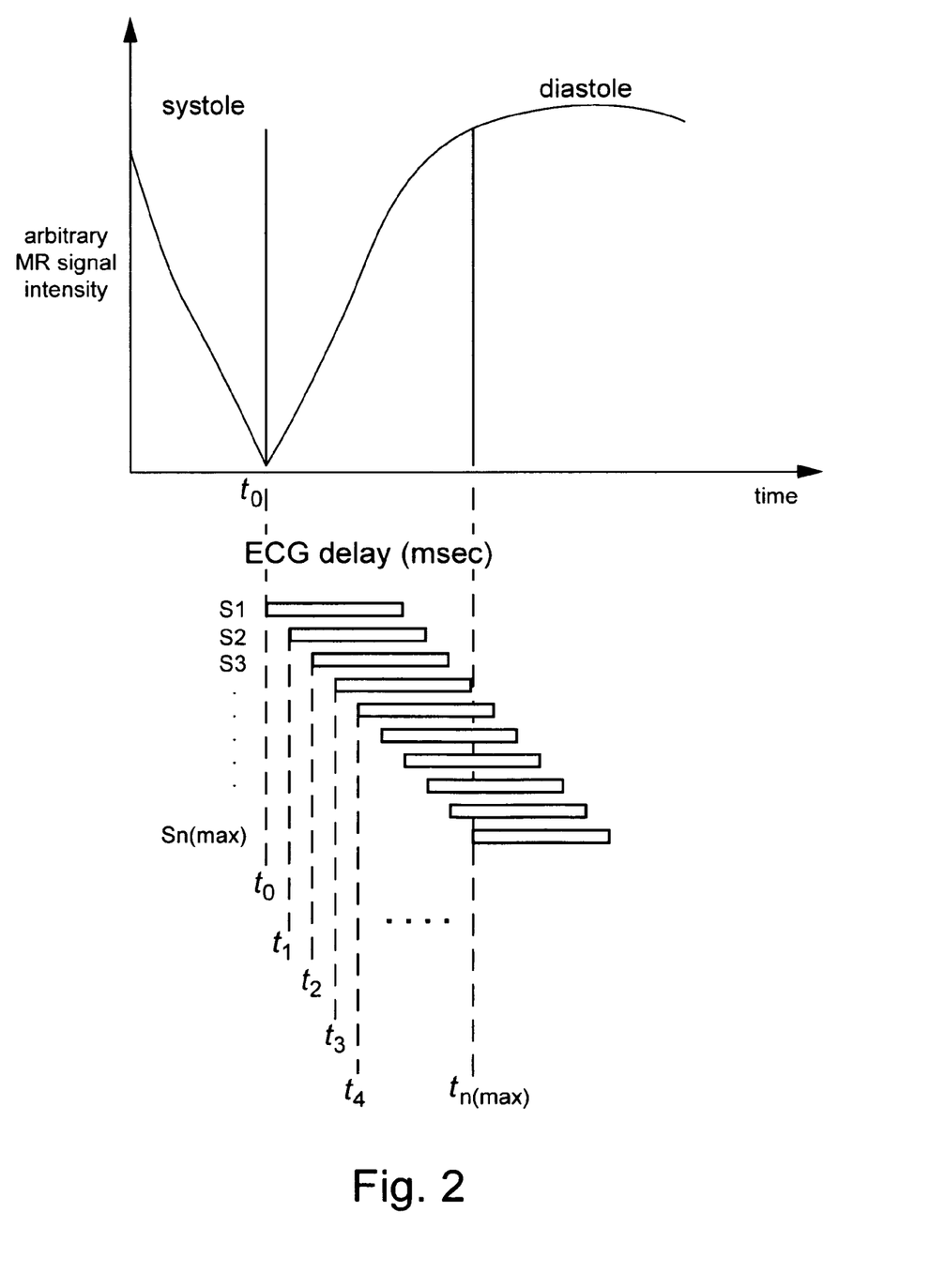
FIG. 2 is an exemplary display showing a timing diagram depicting successive cardiac-gated MR slice imaging sequences with respect to systole and diastole phases of the cardiac cycle in an exemplary embodiment.

For systole to diastole difference images:

Using a FASE (or FBI) sequence, if the phase-encode (PE) direction is perpendicular to the peripheral vessel flow, MR signal intensity of each FASE image with small increments therebetween (such as 1RR to nRRs) will vary as shown in FIG. 2 (which includes a graph of acquired MR signal intensity as a function of time during a cardiac cycle that can be displayed to the user for assistance in designating at least two different acquired images for use in generating a fluid velocity measurement).

Figure 3:
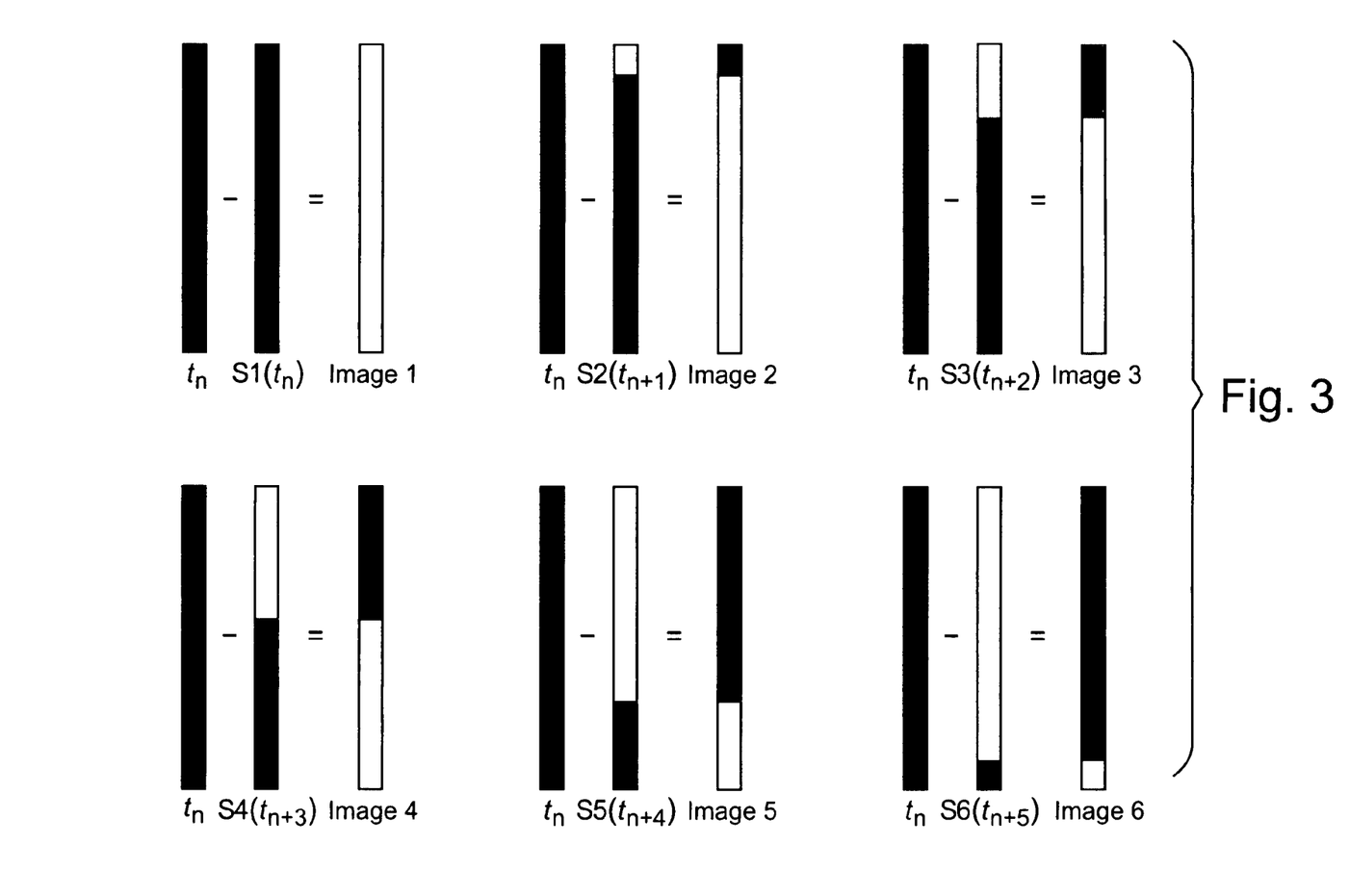
FIG. 3 is a schematic diagram depicting successive difference images obtained by the differences between a "dark" systole image and "bright" diastole images at successive cardiac-gated time increments as depicted in FIG. 2.

Subtraction of lower intensity signals (e.g., in a systole period image) from higher intensity signals (e.g., at a diastolic-triggered period image) will provide a resultant image of a flowing volume that appears like a moving object, as shown in FIG. 3.

If displayed in cine, non-contrast time-resolved MRA can be seen. By tracking the MR flow signal along even tortuous vessels, the vessel length traveled divided by the difference in time between images gives velocity. The average of specific (incremental) flow velocities v1, v2, ... vn gives a mean flow velocity (which can, of course, also be directly calculated if desired without calculating any intermediate specific velocity).

Using time-SLIP BBTI difference images:

Flow-out (non-selective and selective pulses) or flow-in (only selective pulse) time-SLIP, as well as alternative acquisition and subtraction (tag-on and off subtraction) also allows measurement of mean velocity:

Using single shot FSE (FASE): Velocity can be calculated using a moved flow volume within the BBTI time (tag to acquisition pulse) and effective TE (TEeff) as flow travel time. Therefore, velocity can be calculated as length (L) of the moved flow divided by (BBTI+TEeff).

Using balanced SSFP: Velocity can be calculated using moved flow within the BBTI time (tag to acquisition pulse) as the flow travel time. Therefore, velocity can be calculated as length (L) of the moved flow divided by BBTI.

Preferably, all calculations are done on the MR image console by selecting an icon of "Velocity" ("mean velocity" and/or "specific velocity"), e.g., with a mouse click.

As those in the art will appreciate, the non-contrast time-SLIP (ASL) technique observes flow fluids by using multiple different BBTI times in MRI sequences.

The exemplary embodiments provide a relatively simple GUI to facilitate velocity measurements (specific and/or mean) instead of requiring such to be calculated off-line using a calculation tool separate from the MRI display system. This provides an easy and quick calculation of mean and/or specific flow velocities.

As depicted in FIG. 2, an FBI/Navi routine or the like may be utilized to obtain successive slice images S1, S2, S3 ... at successively delayed times from systole towards diastole in the typical PQRSTU cardiac cycle. One complete cardiac cycle is sometimes referred to as an "R-R" cycle. Of course, the frequency of R cardiac pulses equates to the patient's pulse rate.

Using cardiac (or peripheral pulse) gating as appropriate, MRI sequences can be imposed on the patient at successively delayed points in the cardiac cycle. As measured from systole at $t_0$, the delay increments for each successive slice S1, S2, ... Sn(max) are depicted in FIG. 2 out to a maximum time at $t_{n(max)}$.

As those in the art will appreciate, difference images can be generated by subtracting one of these images from the other on a pixel-by-pixel basis. To obtain the maximum contrast in MRA, typically the systole image having minimum signal intensity will be subtracted from the diastole image having the maximum signal intensity so as to produce a single MRA image.

However, if the successive images S2, S3, etc., are subtracted from the systole image S1, a succession of difference images will be produced which can depict a leading edge of a pulsatile fluid flow almost as an advancing "object" along a patient's artery.

FIG. 3 is a schematic depiction of an idealized entirely linear artery that has been imaged at time $t_n$ at systole and then successively imaged again at incrementally increasing time intervals towards diastole at $t_{n+1}$, $t_{n+2}$, etc. The resulting sequence of images starts with a null Image1 (since two identical images are being subtracted) and then progresses to reveal a flowing fluid in the imaged artery section starting from the top and progressing towards the bottom (in FIG. 3) as the flowing fluid produces ever-increasing MR signal intensity because the image times approach more closely to diastole. In effect, one can discern a leading edge of flowing fluid starting from time $t_n$ and traversing various lengths of the artery segment through the different successive time intervals involved.

Figure 4:
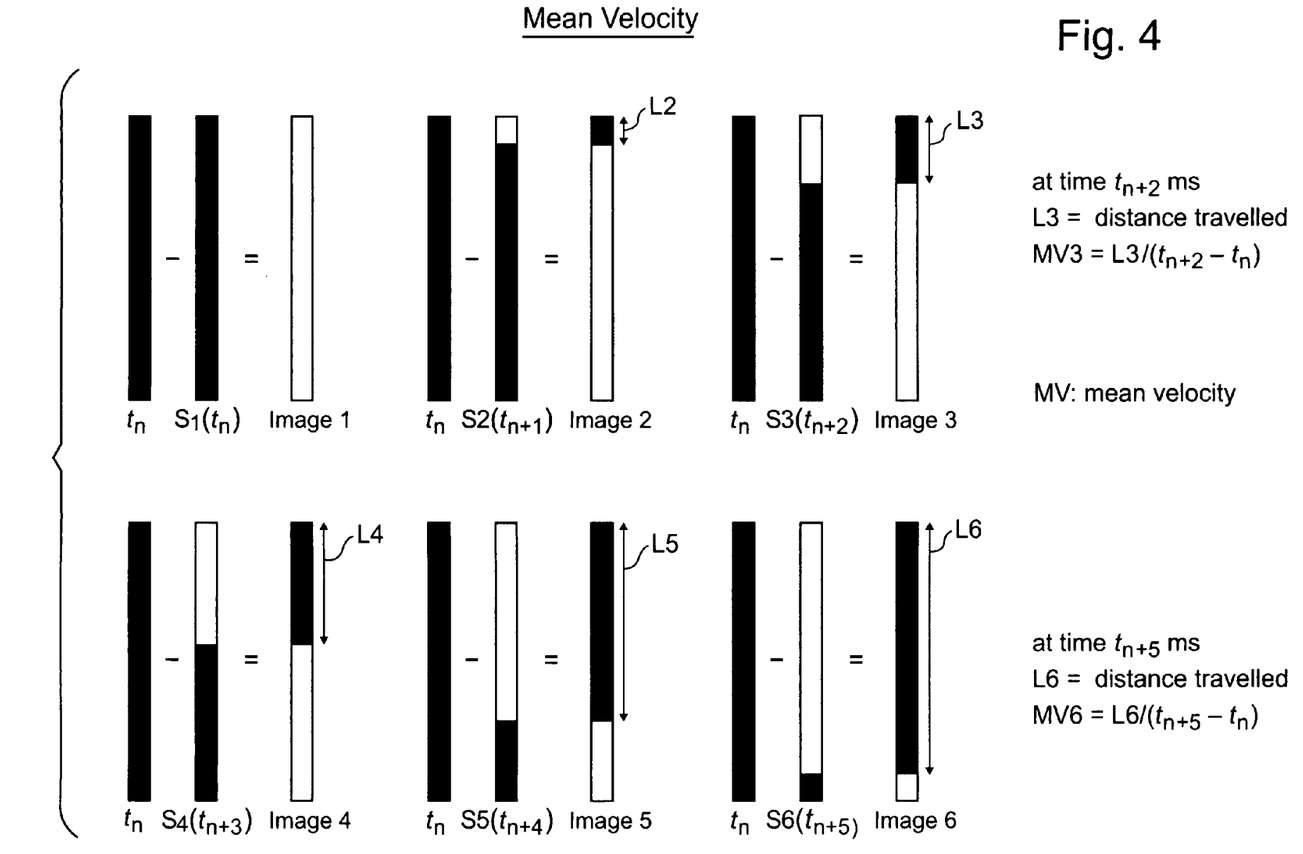
FIG. 4 is a schematic diagram similar to that of FIG. 3, but including annotations explaining how average or mean blood flow velocity can be calculated in accordance with an exemplary embodiment.

Thus, as depicted in FIG. 4, it is possible to measure the lengths of distance traveled by the flowing fluid at the end of each successive time interval—and to divide that length by the elapsed time so as to provide a mean velocity measurement at the end of each image interval.

Figure 5:
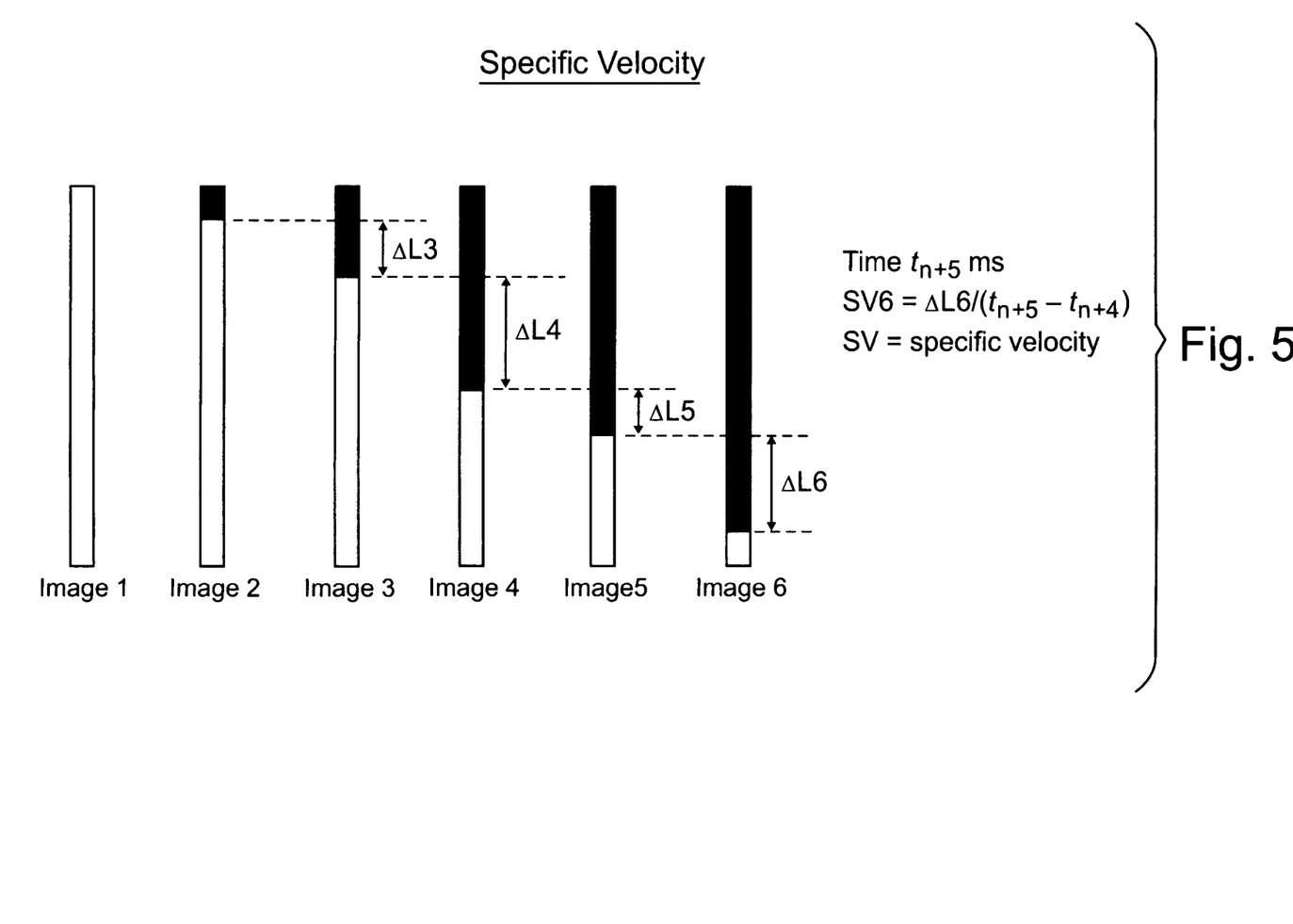
FIG. 5 is a similar schematic diagram showing the difference images from FIGS. 3-4, but now with annotations depicting how specific velocity can be calculated at each successive time interval in accordance with an exemplary embodiment.

Alternatively, as depicted in FIG. 5, a specific velocity for each incremental time interval between images can also be calculated by calculating the incremental distance traveled between images and dividing by the appropriate related time interval. Assuming that the time interval between images is equal, it will thus be seen in FIG. 5 that the specific velocity increases at Image3 compared to Image2, and again at Image4 compared to Image3. However, it appears to decrease at Image5 compared to Image4 and then to increase again at Image6 compared to Image5.

Figure 6:
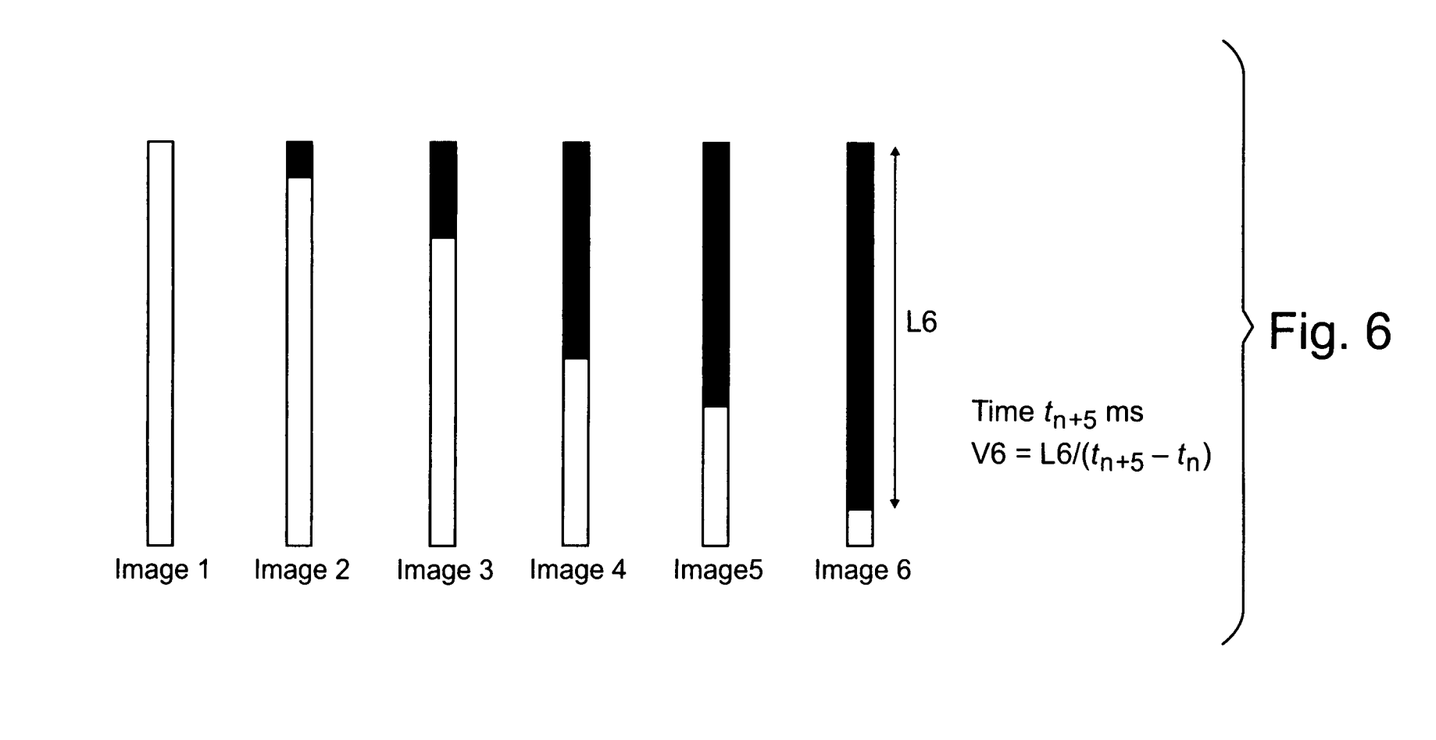
FIG. 6 is similar to FIG. 5, but now demonstrating how an overall average or mean velocity can be calculated over the entire sequence of difference images in an exemplary embodiment.

As depicted in FIG. 6, the same set of successive Images 1-6 can also be analyzed so as to calculate only the average or mean velocity over the entire interval (comparing Image6 to Image1).

In effect, as displayed in cine mode, using diastolic-systolic images, non-contrast time-resolved MRA can now include flow velocity measurements. By tracking the flowing signal source, even along tortuous vessels, the length of the vessel segment traveled divided by the time required for such travel gives a velocity (either average or mean velocity over a succession of intervals and/or a succession of specific velocities if measured between intervals or smaller groups of intervals). That is, the average of the incremental specific velocities from one period to the next gives a mean or average velocity over the longer time period encompassing all of the images.

Figure 7:
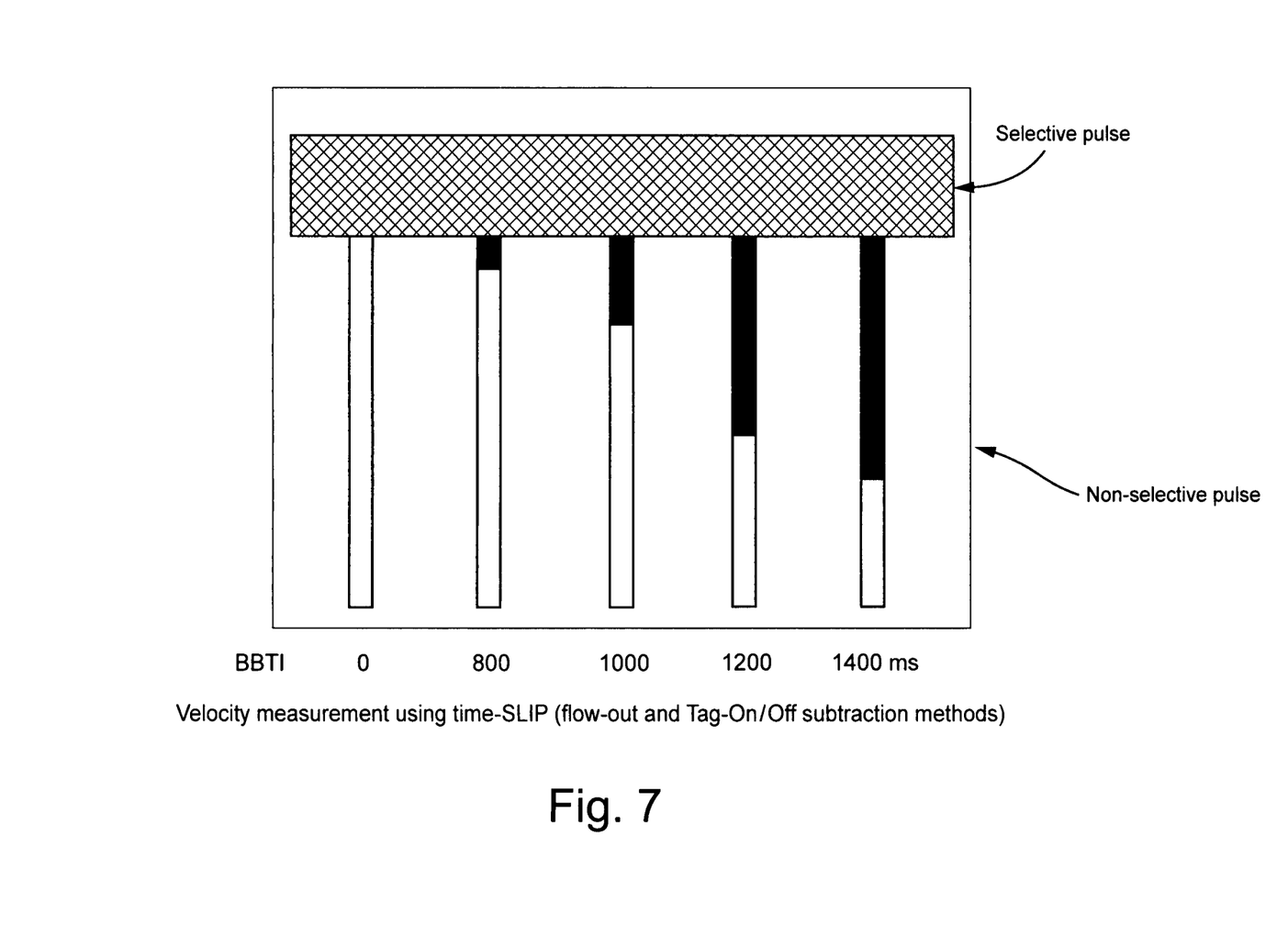
FIG. 7 schematically depicts velocity measurements in accordance with another exemplary embodiment using time-SLIP (spatial labeling inversion pulse) subtraction methods (flow-out and tag-on/off subtraction methods)

FIG. 7 schematically depicts time-SLIP non-contrast imaging of fluid flows. The selective and non-selective pulses are represented by differently sized rectangles. As those in the art will appreciate, by using different BBTI intervals, one can achieve successive images of fluid flows within arteries, veins, etc., similar to the successive images at different time increments described in earlier figures for diastolic-systolic difference images. As should be apparent, measurement of traveled distances along arteries, veins, etc., and dividing by the associated travel times can also produce velocity measurements using this non-contrast flow imaging technique.

Figure 8:
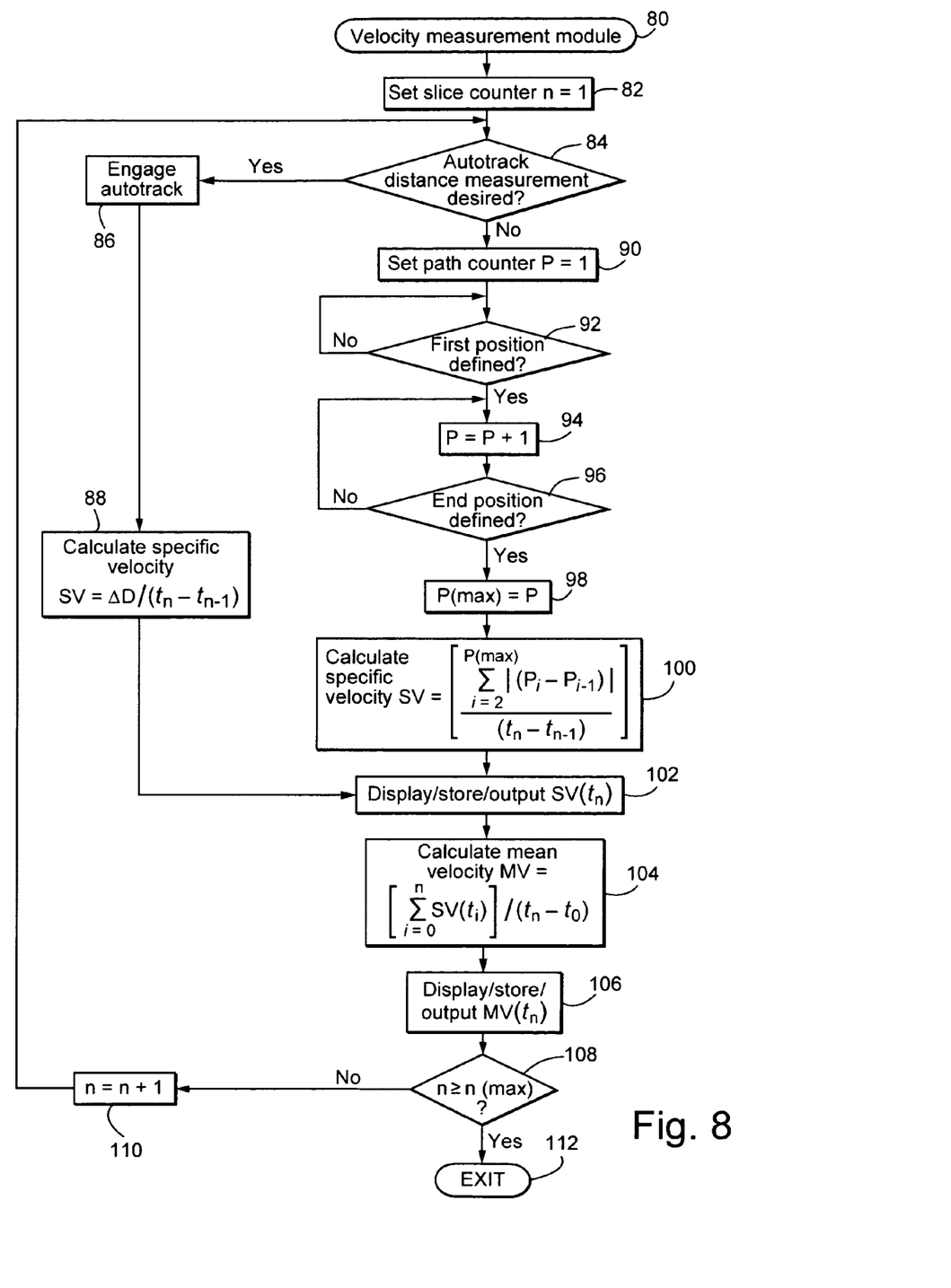
FIG. 8 is a schematic flow chart for an exemplary computer program code structure that may be utilized in an exemplary embodiment.

FIG. 8 schematically depicts a velocity measurement module of computer program code structure. The module may be entered at 80 by any suitable means (e.g., by an operator using mouse clicks on a suitably displayed icon or menu, finger-actuated inputs on a touch-sensitive screen, keyboard inputs, etc.) associated with a main or supervisory operating system or the like.

At 82, a slice counter n is initialized with a value of 1. At 84, a test is made to see whether an option has been set for system auto-track of distance measurements (e.g., by setting a control parameter in a preferences dialog or the like to use an automatic machine-implemented distance tracking algorithm). If so, then the auto-track feature is engaged at 86 and a specific velocity SV is calculated between slices taken at $t_{n-1}$ and subsequently at $t_n$ at 88.

Figure 9:
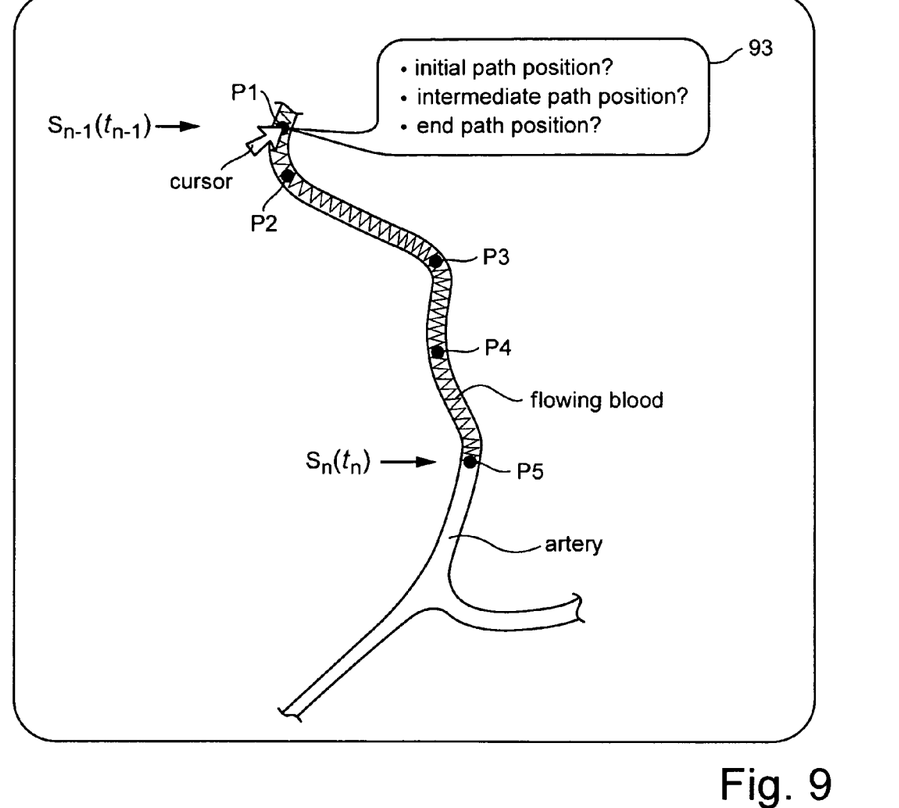
FIG. 9 is a schematic depiction of a possible operator screen appearance utilized during operator definition of successive path position points for blood flow along a tortuous path between two successive image times.

If the auto-track feature is not desired, then at 90, the path counter p is initialized at a value of 1. Thereafter, at 92, a wait loop is entered for the operator to define a first position. For example, as shown at FIG. 9, the operator may move a cursor onto the first point p1 (associated with image time $t_{n-1}$) and click a predetermined mouse button so as to define a first position on a displayed image of fluid flow in an artery or the like. A pop-up menu 93 may also be provided giving the operator a choice of identifying a particular defined point as being an initial path position, an intermediate path position, or an end path position. As depicted, for example, in FIG. 9, five operator-defined points p1-p5 have been defined at strategic points along a tortuously curved vessel (between image times $t_{n-1}$ and $t_n$) such that straight line segments between the identified points along the path of flow will closely approximate the distance of flow from slice image Sn−1 to slice image Sn. Once a first position has been defined at 92 (in FIG. 8), the path counter p is incremented at 94 as shown in FIG. 8. Thereafter, wait loop 96 is entered as additional positions along the path are operator-defined and the path counter is incremented until an end position has been defined. At that point, the maximum value for the path parameter p(max) is defined at 98 as the then-current value of the path counter and the specific velocity SV is then calculated at 100 for that increment of flow between successive slice images Sn and Sn−1.

At 102, the specific velocity SV (no matter how calculated) associated with the ending time $t_n$ is then displayed, stored or otherwise output (e.g., to a remote site as may be desired and configured in a preference section of the system). A running mean velocity MV is then calculated at 104 and, at 106, is similarly displayed, stored or otherwise output as may be desired (e.g., as configured earlier in the system). At 108, a test is made to see if the slice counter has yet reached the end (i.e., slice Sn(max)). If not, then the slice counter is incremented at 110 and control is passed back either to the decision block 84 as depicted in FIG. 8 or directly to a re-initialization of the path counter at block 90 (i.e., if one desires not to give the operator another chance to engage the auto-track system). When all of the available slice data has been processed, then exit of this module is taken at 112 as depicted in FIG. 8.

Figure 10:
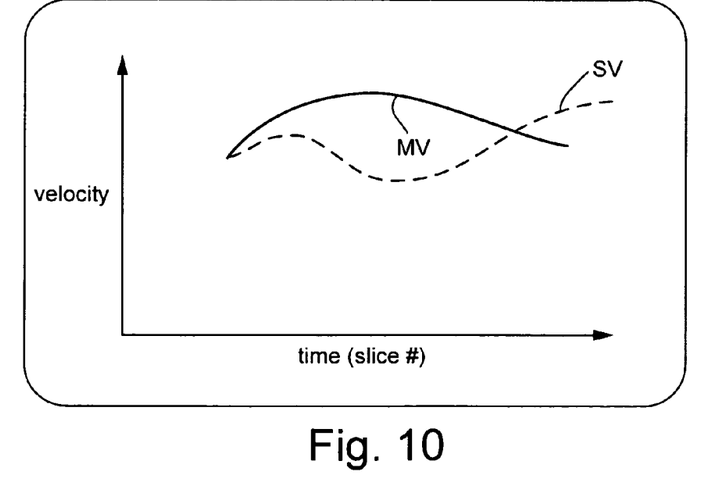
FIG. 10 is a schematic depiction of a possible output display graph of specific velocity and/or mean velocity versus time and/or slice position that may be facilitated by the exemplary embodiment.

As depicted in FIG. 10, the specific velocity SV and/or running mean velocity MV may be graphically displayed as a function of time (or slice number or the like).

While certain embodiments of the inventions have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer-implemented method for measuring velocity of MR-imaged fluid flows, said method comprising use of at least one programmed computer to:
   generate data representing at least two measures of distance traveled by flowing fluid appearing in at least three MR images of a subject's tissue taken at different respective imaging times, by calculating incremental distances between adjacent ones of said MR images;
   generate data representing each specific velocity of said flowing fluid in each interval by calculating at least two incremental distances traveled by said fluid divided by elapsed time during said travel respectively based on said different respective imaging times of said at least three MR images; and
   output said data representing each specific velocity to at least one of: (a) a display screen, (b) a non-transitory data storage medium, and (c) a remotely located site, wherein
   said MR-images are acquired by fresh blood imaging (FBI) using cardiac gating and successive image slices are each acquired within a single cardiac cycle;
   a graph of acquired MR signal intensity as a function of time during a cardiac cycle is displayed to the user; and
   a user control input is accepted for use in automatically generating said data representing at least one fluid velocity measurement.

2. A computer-implemented method as in claim 1, wherein:
   data representing a mean velocity is measured by calculating a cumulative distance traveled by said fluid over a plurality of successive imaging times divided by a cumulative elapsed time during said cumulative travel based on said different respective imaging times.

3. A computer-implemented method as in claim 1, wherein said measure of distance traveled between different respective MR-imaging times is generated by:
   displaying MR-images taken at different respective imaging times;
   accepting user-specified locations on the displayed images as the therein current position of a given volume of flowing fluid; and
   automatically calculating distance(s) between said specified locations as a measure of distance(s) traveled by the imaged flowing fluid.

4. A computer-implemented method as in claim 1, wherein said measure of distance traveled between different respective MR-imaging times is generated by:
   automatically determining distance of an imaged fluid volume displacement between MR-imaging times.

5. A computer-implemented method as in claim 4, wherein fluid velocity measurement is triggered by a user control input.

6. A computer-implemented method as in claim 1, wherein said imaging times are triggered by the subject's cardiac cycle, at least one of said MR-images being taken substantially at systole in the subject's cardiac cycle and at least one of said MR-images being taken substantially at diastole in the subject's cardiac cycle and wherein:
   a distance of fluid movement between systole and diastole is automatically generated based on subtraction of diastolic and systolic MR-images to create an MR angiographic (MRA) image; and
   a user control input triggers generation of corresponding fluid flow velocity measurement data and display of same to the user.

7. A computer-implemented method as in claim 1, wherein:
   said MR-images are acquired using a Time-Spatial Labeling Inversion Pulse (Time-SLIP) with Fast Asymmetric Spin Echo (FASE) sequence; and
   elapsed time is based on BBTI (black-blood time to inversion) plus TEeff.

8. A computer-implemented method as in claim 1, wherein:
   said MR-images are acquired using a Time-SLIP with bSSFP sequence using centric ordering of k-space phase encoding; and
   elapsed time is based on BBTI.

9. A computer-implemented method as in claim 1, wherein:
   said MR-images are acquired using a Time-SLIP with bSSFP sequence using sequential ordering of k-space phase encoding; and
   elapsed time is based on BBTI+ETL/2.

10. Apparatus for measuring velocity of MR-imaged fluid flows, said apparatus comprising:
    means for displaying a graph of acquired MR signal intensity of a plurality of acquired MR images as a function of time during a cardiac cycle;
    means for accepting user control input for use in generating data representing fluid velocity measurements; and
    at least one programmed computer including:
       means for generating data representing at least two measures of distance traveled by flowing fluid appearing in at least three MR images of a subject's tissue taken at different respective imaging times, by calculating incremental distances between adjacent ones of said MR images;
       means for automatically generating data representing each specific velocity of said flowing fluid in each interval by dividing said at least two incremental distances traveled by elapsed time during said travel respectively based on said different respective imaging times of said at least three MR images; and means for outputting said data representing each specific velocity to at least one of: (a) said means for displaying, (b) a non-transitory data storage medium, and (c) a remotely located site wherein said MR-images are acquired by fresh blood imaging (FBI) using cardiac gating and successive image slices are each acquired within a single cardiac cycle.

11. Apparatus as in claim 10, wherein:

data representing a mean velocity is measured by calculating a cumulative distance traveled by said fluid over a plurality of successive imaging times divided by a cumulative elapsed time during said cumulative travel based on said different respective imaging times.

12. Apparatus as in claim 10, wherein said measure of distance traveled between different respective MR-imaging times is generated by:

displaying MR-images taken at different respective imaging times;

accepting user-specified locations on the displayed images as the therein current position of a given volume of flowing fluid; and automatically calculating distance(s) between said specified locations as a measure of distance(s) traveled by the imaged flowing fluid.

13. Apparatus as in claim 10, wherein said measure of distance traveled between different respective MR-imaging times is generated by:

automatically determining distance of an imaged fluid volume displacement between MR-imaging times.

14. Apparatus as in claim 13, wherein fluid velocity measurement is triggered by a user control input.

15. Apparatus as in claim 10, wherein said imaging times are triggered by the subject's cardiac cycle, at least one of said MR-images being taken substantially at systole in the subject's cardiac cycle and at least one of said MR-images being taken substantially at diastole in the subject's cardiac cycle and wherein:

a distance of fluid movement between systole and diastole is automatically generated based on subtraction of diastolic and systolic MR-images to create an MR angiographic (MRA) image; and a user control input triggers generation of corresponding fluid flow velocity measurement data and display of same to the user.

16. Apparatus as in claim 10, wherein:

said MR-images are acquired using a Time-Spatial Labeling Inversion Pulse (Time-SLIP) with Fast Asymmetric Spin Echo (FASE) sequence; and elapsed time is based on BBTI (black-blood time to inversion) plus TEeff.

17. Apparatus as in claim 10, wherein:

said MR-images are acquired using a Time-SLIP with bSSFP sequence using centric ordering of k-space phase encoding; and elapsed time is based on BBTI.

18. Apparatus as in claim 10, wherein:

said MR-images are acquired using a Time-SLIP with bSSFP sequence using sequential ordering of k-space phase encoding; and elapsed time is based on BBTI+ETL/2.

* * * * *